(12) United States Patent
Planard-Luong et al.

(10) Patent No.: US 10,524,556 B2
(45) Date of Patent: Jan. 7, 2020

(54) DEVICE FOR PACKAGING AND DISPENSING A PRODUCT

(71) Applicant: SEB S.A., Ecully (FR)

(72) Inventors: Thi Hong Lien Planard-Luong, Bures sur Yvette (FR); Franck Mandica, Francheville (FR); Johan Sabattier, Mornant (FR); Régis Fereyre, Lyons (FR)

(73) Assignee: SEB S.A., Ecully (FR)

( * ) Notice: Subject to any disclaimer, the term of this patent is extended or adjusted under 35 U.S.C. 154(b) by 16 days.

(21) Appl. No.: 16/061,619

(22) PCT Filed: Dec. 6, 2016

(86) PCT No.: PCT/EP2016/079932
§ 371 (c)(1),
(2) Date: Jun. 12, 2018

(87) PCT Pub. No.: WO2017/102458
PCT Pub. Date: Jun. 22, 2017

(65) Prior Publication Data
US 2019/0335880 A1 Nov. 7, 2019

(30) Foreign Application Priority Data
Dec. 17, 2015 (FR) .................... 15 62617

(51) Int. Cl.
*B43K 5/04* (2006.01)
*A45D 34/04* (2006.01)
(Continued)

(52) U.S. Cl.
CPC .......... *A45D 34/041* (2013.01); *A61N 1/325* (2013.01); *A61N 1/328* (2013.01); *A45D 2034/005* (2013.01)

(58) Field of Classification Search
CPC ...... A61N 1/325; A61N 1/328; A45D 34/041; A45D 2034/005
(Continued)

(56) References Cited

U.S. PATENT DOCUMENTS 1,776,137 A 9/1930 Strouse
4,157,771 A 6/1979 Smith
(Continued)

FOREIGN PATENT DOCUMENTS

DE 23 23 762 A1 11/1974
EP 0 539 667 A1 5/1993

OTHER PUBLICATIONS

International Preliminary Report on Patentability and the Written Opinion of the International Searching Authority as issued in International Patent Application No. PCT/EP2016/079932, dated Jun. 19, 2018.
(Continued)

*Primary Examiner* — Jennifer C Chiang
(74) *Attorney, Agent, or Firm* — Pillsbury Winthrop Shaw Pittman LLP

(57) ABSTRACT

A packaging and distribution device, for example a device for treatment with an electric current, includes: a refill containing a product to be distributed, including a vessel defined at least partially by a flexible wall; a pressing member for pressing on the flexible wall in order to apply pressure to the product contained therein, wherein the pressing member includes two flaps hingedly connected to one another, each connected to a mechanical system biasing the flap to bear against the refill.

17 Claims, 5 Drawing Sheets

Figure 1:
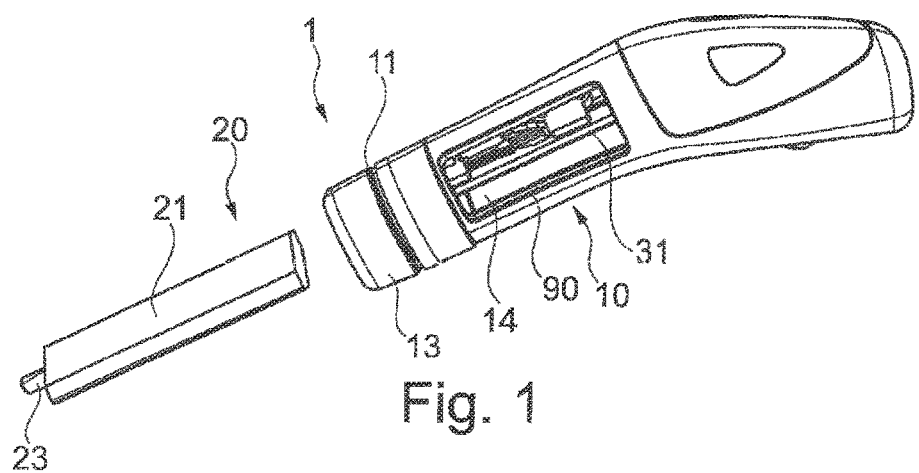

(51) Int. Cl.
*A61N 1/32* (2006.01)
*A45D 34/00* (2006.01)

(58) Field of Classification Search
USPC .............................. 401/152, 155, 156, 158
See application file for complete search history.

(56) References Cited

U.S. PATENT DOCUMENTS

| | | | |
|---|---|---|---|
| 5,281,202 A | 1/1994 | Weber et al. | |
| 2016/0310728 A1* | 10/2016 | Cazares Delgadillo | ..................... A61N 1/303 |
| 2018/0353747 A1* | 12/2018 | Planard-Luong | ...... A45D 34/00 |
| 2019/0000211 A1* | 1/2019 | Planard-Luong | ...... A61N 1/303 |

OTHER PUBLICATIONS

International Search Report as issued in International Patent Application No. PCT/EP2016/079932, dated Feb. 20, 2017.

* cited by examiner

DEVICE FOR PACKAGING AND DISPENSING A PRODUCT

CROSS-REFERENCE TO RELATED APPLICATIONS

This application is the U.S. National Stage of PCT/EP2016/079932 filed Dec. 6, 2016, which in turn claims priority to French patent application number 1562617 filed Dec. 17, 2015. The content of these applications are incorporated herein by reference in their entireties.

This invention concerns packaging and dispensing devices comprising a refill containing a product to be dispensed, and more specifically iontophoresis devices.

It is known to package a product in a flexible pouch and subject it to the action of a pressing member to force the product to flow out of the pouch under the effect of the pressure exerted by the pressing member.

EP 0539667 A1 describes a device for emptying a flexible pouch comprising a toggle mechanism to bias a pressure plate to move in contact with the pouch. The interest of such a mechanism is that it achieves substantially constant pressure, regardless of how empty the pouch is.

U.S. Pat. No. 4,157,771 discloses another example of an emptying device, also with a toggle mechanism, with a pressure plate guided so as to be displaceable by four guides.

U.S. Pat. No. 1,776,137 describes an emptying device arranged to act on a tube of toothpaste; the latter is held between two pressure plates connected to one another by a toggle mechanism. Unlike the devices described in the publications EP 0539667 A1 and U.S. Pat. No. 4,157,771, no return spring is provided to bias the pressure plates to move, and the latter are biased only when the user acts on them.

Further improvement is needed in packaging and dispensing devices in order to apply pressure to the contents of a refill and use this pressure to dispense the contents thereof.

In particular, there is interest in a device that would be particularly reliable, compact, and relatively inexpensive to produce, and would allow the refill to be emptied in a satisfactory manner.

The invention achieves this objective through a packaging and dispensing device, preferably a device for treatment with an electric current, comprising:
  a refill containing a product to be dispensed, comprising a container defined at least partially by a flexible wall,
  a pressing member for pressing on the flexibly: wall in order to apply pressure to the product contained therein, characterized in that the pressing member comprises two flaps hingedly connected to one another, each connected to a mechanical system biasing the flap to bear against the refill.

In the invention, the use of at least two presser flaps hingedly connected to one another allows the refill to be emptied properly using a compact design. The two flaps can be biased to pivot in relation to one another in the direction of closure of the angle between them, which may, drive the product toward the median axis of the refill, and facilitate the evacuation of its contents.

Preferably, the flaps comprise guide reliefs at their front and back ends, which cooperate with the rest of the device. These guide reliefs are preferably made in the form of pins molded of thermoplastic material with the flaps.

Each flap may comprise a pin that cooperates with a corresponding relief during the descent of the flap accompanying the emptying of the pouch. This cooperation tends to make the flap pivot as it approaches the other flap. The pin preferably bears against the outer periphery of a ring which defines an opening through which is engaged an outflow cannula for the refill product.

In particular, each flap can advantageously comprise a pin at the front and a pin at the back, which are guided in the corresponding slots during the descent phase, to ensure that the refill is emptied as well as possible.

When the flaps descend, they tend to draw back, that is, they move away from the opening above; the pins, bearing against the ring, may promote a forward and upward tilt of the flaps, favoring a complete emptying of the refill.

Once the flaps have drawn back sufficiently, the pins stop coming into contact with the ring, and the flaps are not constrained by the latter in their orientation.

The mechanical system preferably comprises, for each flap, a slider biased to move along an axis by a spring and a link hingedly connected at its ends to the slider and to the flap, respectively, such that movement of the slider along the said axis, tending to increase the angle of the link with the latter, is accompanied by pressure applied by the link to the flap.

The two sliders may be connected to one another by a common axle serving as an articulation for the two links. This axle may be snap-fitted at each of its ends into a slider housing open in an opposite direction to the spring. The springs are preferably helical and engaged on rods on which the sliders move.

The refill may be elongated along a longitudinal axis and the flaps are preferably hingedly connected to one another around a geometric hinge axis substantially parallel to the longitudinal axis of the refill. Iii particular, the two flaps can each be hingedly connected to a pivoting support element, which may pivot to accompany the movement of the flaps. This pivoting support element and the link together complete the toggle mechanism, and the pivoting support element is advantageously formed of a branch provided at the end of a hook used as an axle to connect the link to the associated flap. The branches may form part of an open loop where the side opposite the branches bears against the bottom of a hook fixed to the device. Preferably, the loop is made of spring wire. Thus, the elastic deformation of the loop permits the flaps to pivot slightly in relation to one another, while biasing the flaps in a predefined rest position.

The refill preferably comprises a flexible pouch defining the aforementioned flexible wall. The refill may comprise a dispensing cannula at the front, as mentioned above.

The device advantageously comprises a case with a housing to hold the refill, and a treatment head by which the product is dispensed. Preferably, the treatment head is removably fixed to the case, and can be withdrawn for installation and removal of the refill.

The refill may contain a cosmetic or dermatological product, preferably an electrical conductor.

The product may be dispensed by selectively opening a passage enabling fluid communication to be established between the inside of the container and at least one outlet opening of the device. Preferably, the device includes a solenoid valve that defines this passage, or a valve that can be activated manually to dispense the product.

Figure 2:
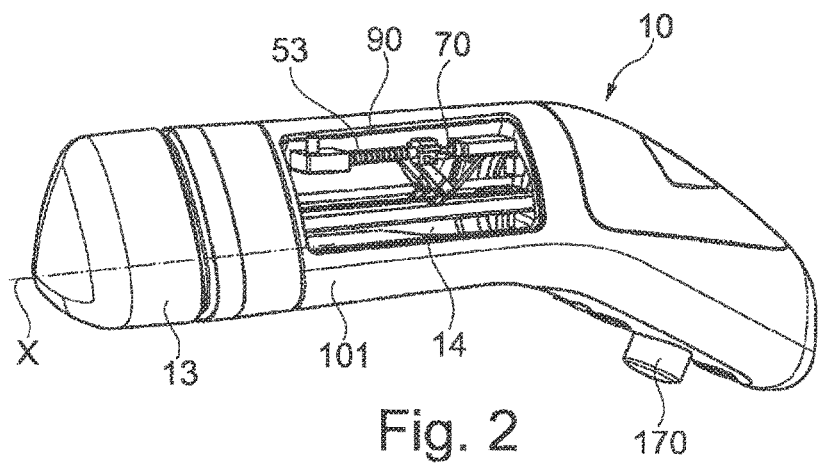
Figure 3:
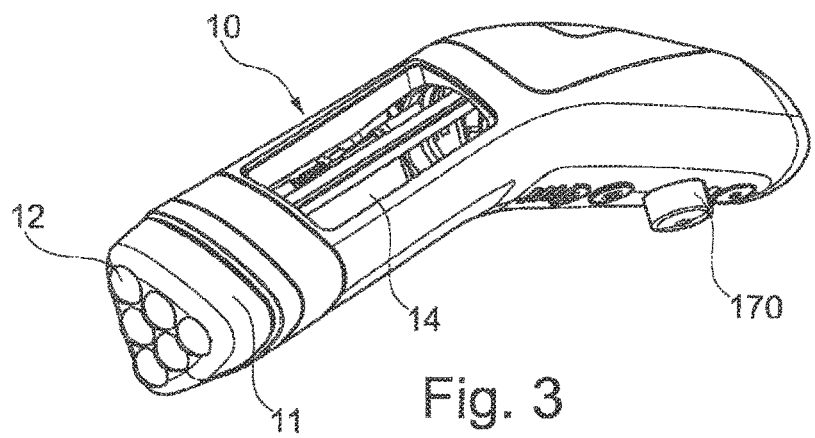
Figure 4:
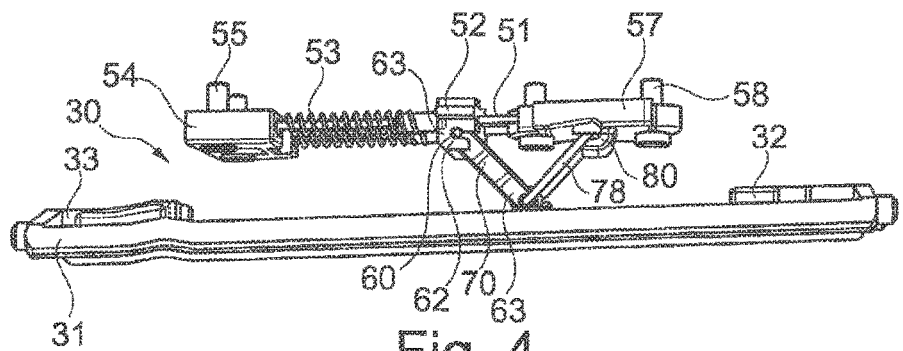
Figure 5:
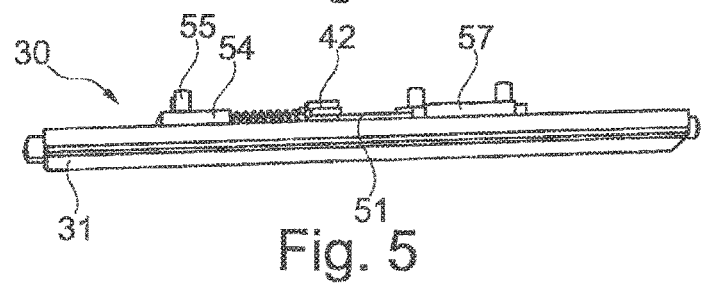
Figure 6:
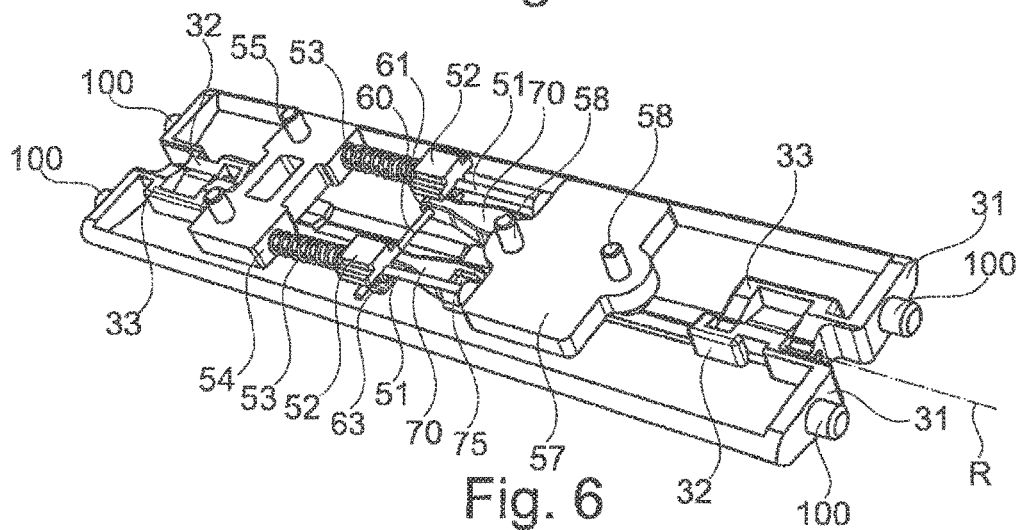
Figure 7:
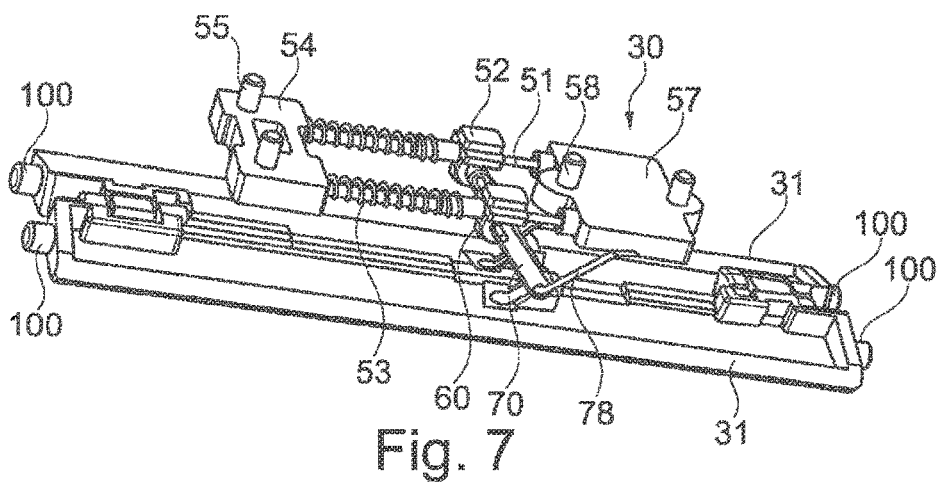
Figure 8:
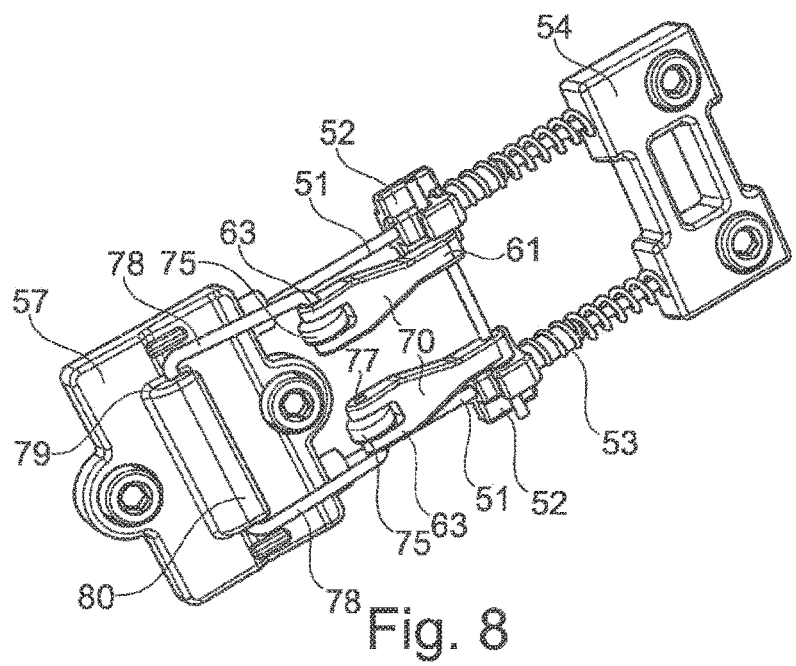
Figure 9:
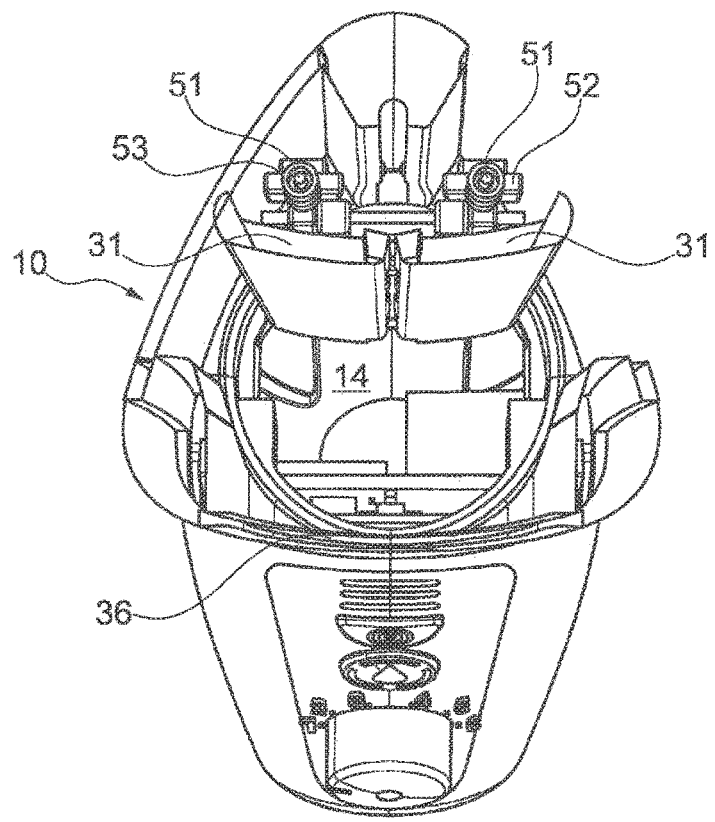
Figure 10:
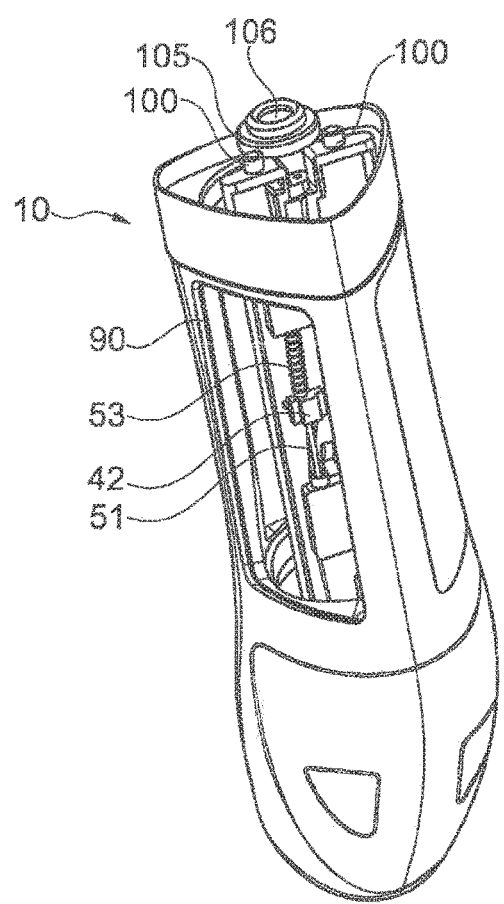
Figure 11:
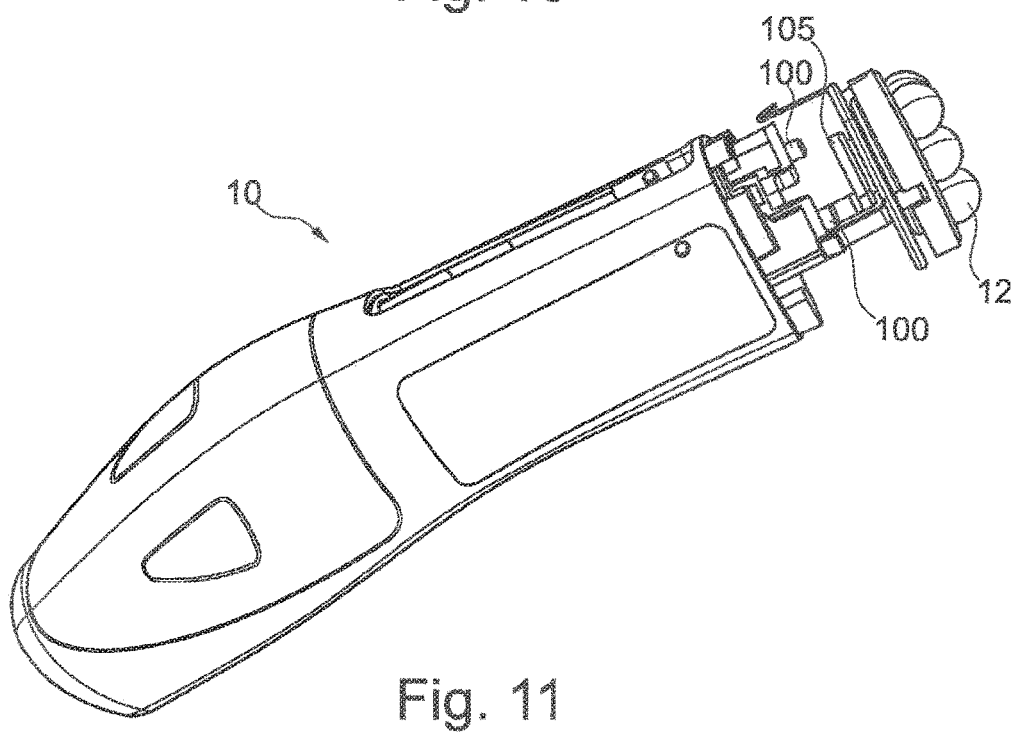
Figure 12:
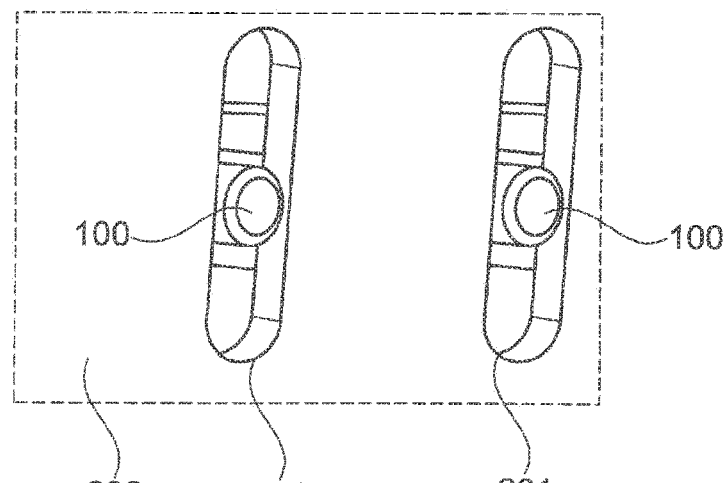

The invention may be better understood by reading the following detailed description of a non-restrictive example implementation, and by examining the attached drawing, in which:

FIG. 1 is a schematic representation of a perspective view of a packaging and dispensing device according to the invention, the refill being represented separately outside of the appliance, FIG. 2 is a perspective view, from another angle, of the appliance in FIG. 1, with the pressing member occupying a different position in FIGS. 1 and 2, FIG. 3 is a view of the appliance after the protective cap has been removed from the treatment head, FIG. 4 represents separately the flaps and the mechanical system biasing the latter to bear against the refill, in a lowered position corresponding to the emptying of the refill, FIG. 5 is a view similar to FIG. 4, in a raised position, the refill being full, FIGS. 6 and 7 are perspective views of the flaps and the mechanical system, FIG. 8 partially represents the mechanical system, FIG. 9 is a cross section of the device, FIGS. 10 and 11 are two perspective views illustrating the movement of the flaps relative to the head of the appliance during emptying of the refill, and FIG. 12 illustrates the guiding of the flaps at the back.

The packaging and dispensing device 1 according to the invention comprises an appliance 10 which holds a refill 20 containing a product to be applied on the region to be treated using the appliance.

In the example considered, the product contained in the refill 20 is a cosmetic or dermatological product and the appliance 10 is an iontophoresis appliance intended for treating human keratin materials using an electric current. For this purpose, the appliance 10 includes, as seen in FIG. 3 in particular, a treatment head 11 comprising in this case a plurality of application balls 12 which make it possible to apply the product on the region to be treated while moving the appliance in contact with it. The appliance 10 may comprise an electronic circuit (not shown) to subject the region to be treated to an electric current simultaneously with the application of the product contained in the refill 20. The appliance may include an electrode in contact with the composition and a counter-electrode held by the user. The composition conducts electricity.

The appliance 10 may comprise, as illustrated, a button 170 to adjust the current intensity and other buttons and/or indicators useful for control of the appliance.

When not being used, the treatment head 11 may be covered with a removable cap 13, as illustrated in FIGS. 1 and 2.

The refill 20 is held inside the appliance 10 in a housing 14 seen in FIG. 9 in particular; for the sake of clarity, the refill 20 is not represented in the figures inside the appliance 10. The case of the appliance has a window 90 that permits access to the housing 14.

The appliance 10 comprises a device 30 for emptying the refill 20 which includes, as shown in particular in FIGS. 4 to 7, two flaps 31, together constituting a pressing member coming into contact with the upper side 21 of the refill 20 when the latter is in place inside the appliance 10. The two flaps 31 are hingedly connected to one another around a geometric hinge axis R which is substantially parallel to the longitudinal axis X of the housing holding the refill 20. The refill is itself elongated around a longitudinal axis which substantially coincides with the longitudinal axis X when the refill 20 is in place inside the appliance 10.

In the example considered, the flaps 31 have male 32 and female 33 hinge elements which permit such an articulation, the hinge elements 32 and 33 being provided at the front and back, respectively, of the flaps 31, that is, close to their longitudinal extremities.

Pins 100 are present at the end of the flaps 31. Their role is explained later in the document.

To bias the pressing member constituted by the flaps 31 to move downwards, that is, toward the wall 36 constituting the bottom of the housing 14 holding the refill 20, a mechanical system is provided. This mechanical system comprise two rods 51, substantially parallel to the longitudinal axis X, on which the sliders 52 move, each under the return effect of a helical spring 53 arranged on the corresponding rod 51. The end of each spring opposite the slider 52 bears against a stop element 54 which is also used as a spacer for the rods 51. This stop element 54 has shafts 55 for holding screws, which permit it to be attached to the body 101 of the case of the appliance 10. The ends of the rod 51 opposite the stop element 54 are held by a part 57 which is also attached to the body of the case by shafts 58, in which screws (not shown) are engaged.

The stop element 54 and the part 57 are attached to one another inside the case 101 during operation of the device 30.

The sliders 52 are connected to one another by an axle 60 which is perpendicular to that of the rods 51 and which, in the example considered, is formed of a metal rod. The latter is snap-fitted into housings 62 formed in wings 63 made by molding material with the sliders 52. The wings 63 extend the sliders 52 under the rods 51.

A link 70 connects each slider 52 to a corresponding flap 31. These links 70 comprise an end 61 which is crossed by the axle 60 and an opposite end 63 which is hingedly connected to the flap 31. The end 63 forms, as seen in FIG. 8 in particular, a clevis fitting between whose branches is engaged a hinge element 75 made of a single part by molding with the corresponding flap 31. The end 63 of each link 70 and the associated hinge element 75 are crossed by a hook 77 formed by angling a branch 78 of a loop in the form of an open frame. The side 79 of the loop opposite the opening is held in a hook 80 molded with the part 57, on its face turned toward the flaps 31. The loop is made from spring wire, which permits the branches 78 to flex slightly in relation to one another and to be able also to make a rotation by twisting the side of the loop held in the hook 80.

Referring to FIGS. 10 and 11, we see that the head 11 comprises a ring 105 defining an opening 106 for inserting the dispensing cannula 23 at the front of the refill 20.

The head 11 has channels that guide the product toward the balls 12 and allows the product to leave the device through the clearance between the balls 12 and their housings.

When the refill 20 is full, the flaps 31 are in a raised position, as illustrated in FIG. 10. The springs 53 are compressed as much as possible, and the flaps 31 are positioned as far forward toward the head 11 as possible.

The pins 100 at the front end are positioned above the ring 105.

The pins 100 situated in the back are engaged in the respective slots 201 of a wall 202 of the device 1, as illustrated in FIG. 12. The slots 201 are parallel with each other and the pins 100 drop inside them while the refill 20 empties.

Preferably, the pins 100 have enough guiding clearance to permit them to pivot easily.

The operation of the device 1 is as follows.

In order to insert the refill 20 into the appliance 10, the user begins by removing the treatment head 11 in order to access the housing 14 from the front. The user attaches the refill 20 on the head 11 by inserting the cannula 23 into the opening 106 of the treatment head, then inserts the refill 20 thus coupled to the treatment head 11 into the housing 14, possibly using the window 90 arranged in the body of the case to first bring the flaps 31 into the raised position.

Once the refill 20 is in place, the flaps 31 press against it and the lower side of the refill bears against the wall 36 defining the bottom of the housing 14, opposite the flaps 31.

The links 70 serve as a toggle mechanism, which makes it possible to maintain substantially constant bearing force of the flaps 31 against the refill 20 while the springs 53 are elongated. Thus, when exiting the refill 20, the product may be dispensed at a substantially, constant rate, when the communication by which the dispensing cannula 53 comes into contact with the dispensing opening or openings is open.

A valve or solenoid valve system, not pictured, permits opening this fluid communication between the inside of the refill and one or more dispensing openings, either in response to the actuation of a dispensing button by the user, or automatically when the appliance determines that such dispensing should be triggered.

The valve system comprises, for example, an opening/closing system in which the product circulates in a flexible conduit and a mechanism flattens the conduit to close it, and moves away from it to allow the product to pass again.

When the refill is inserted, the dispensing system is closed so that product cannot exit accidentally, even if the user presses on the refill with his fingers.

The appliance comprises a plug connected either to the outflow cannula 23 of the refill 20 or connected to the end which opens at the user's command. For example, the plug comprises a pressurizing flap using a spring. The flap may be drawn back by pressing a button opposite the spring permitting the flap to draw back, which allows the formula to pass. The volume of the refill 20 is, for example, between 10 and 20 ml, but the invention is not limited to this volume range.

The thickness of the refill which must be compressed by the flaps 31, is, for example, between 9 and 13 mm, and the course of the flaps 31 during their descending movement, in the absence of the refill 20, is preferably greater.

The invention claimed is:

1. A packaging and dispensing device, preferably a device for treatment with an electric current, comprising:
    a refill containing a product to be dispensed, comprising a container defined at least partially by a flexible wall, and
    a pressing member for pressing on the flexible wall in order to apply pressure to the product contained therein,
wherein the pressing member comprises two flaps hingedly connected to one another, each connected to a mechanical system biasing the flap to bear against the refill.

2. The packaging and dispensing device according to claim 1, wherein the mechanical system comprises for each flap a slider biased to move along an axis by a spring and a link hingedly connected at its ends to the slider and to the flap, respectively, such that movement of the slider along the axis, tending to increase an angle of the link with the axis, is accompanied by pressure applied by the link to the flap.

3. The packaging and dispensing device according to claim 2, wherein the two sliders are connected to one another by a common axle serving as an articulation for the two links.

4. The packaging and dispensing device according to claim 3, the common axle is snap-fitted into a slider housing open in an opposite direction to the spring.

5. The packaging and dispensing device according to claim 2, wherein the springs are helical and engaged on rods on which the sliders move.

6. The packaging and dispensing device according to claim 1, wherein the refill is elongated along a longitudinal axis and the flaps are hingedly connected to one another around a geometric hinge axis parallel to the longitudinal axis of the refill.

7. The packaging and dispensing device according to claim 1, wherein the two flaps are each hingedly connected to a pivoting support element, which is pivotable to accompany the movement of the flaps.

8. The packaging and dispensing device according to claim 7, wherein the pivoting support element is formed of a branch provided at the end of a hook used as an axle to connect the link to the associated flap.

9. The packaging and dispensing device according to claim 8, wherein the branches form part of an open loop where the side opposite the branches bears against the bottom of a hook fixed to the device.

10. The packaging and dispensing device according to claim 1, wherein the loop is made of spring wire.

11. The packaging and dispensing device according to claim 1, wherein the refill comprises a flexible pouch defining the flexible wall.

12. The packaging and dispensing device according to claim 1, wherein the refill comprises a dispensing cannula at the front.

13. The packaging and dispensing device according to claim 1, comprising a case with a housing to hold the refill, and a treatment head by which the product is dispensed.

14. The packaging and dispensing device according to claim 13, wherein the treatment head is removably fixed to the case, and able to be withdrawn for installation and removal of the refill.

15. The packaging and dispensing device according to claim 1, wherein the flaps comprises at their front and back ends guide reliefs which cooperate with the rest of the device, these reliefs being made in the form of pins molded of thermoplastic material with the flaps.

16. The packaging and dispensing device according to claim 1, wherein the refill comprises a cosmetic or dermatological product.

17. The packaging and dispensing device according to claim 15, wherein the back pins are guided into corresponding slots.

* * * * *